United States Patent
Jones et al.

(10) Patent No.: US 7,232,485 B2
(45) Date of Patent: Jun. 19, 2007

(54) METHOD OF DETERMINING CRYSTALLIZATION

(75) Inventors: Gareth Jones, Warrington, WA (US); Neville John Freeman, Tarporley (GB); Gerard Anthony Ronan, Salford (GB); Marcus Swann, Lymm (GB); Attia Boudjemline, Manchester (GB)

(73) Assignees: Council for The Central Laboratory Of The Research Councils, Warrington (GB); Farfield Sensors Limited, Manchester (GB)

( * ) Notice: Subject to any disclaimer, the term of this patent is extended or adjusted under 35 U.S.C. 154(b) by 0 days.

(21) Appl. No.: 10/478,159

(22) PCT Filed: May 20, 2002

(86) PCT No.: PCT/GB02/02185

§ 371 (c)(1),
(2), (4) Date: Jun. 29, 2004

(87) PCT Pub. No.: WO02/095380

PCT Pub. Date: Nov. 28, 2002

(65) Prior Publication Data

US 2004/0245475 A1    Dec. 9, 2004

(30) Foreign Application Priority Data

May 18, 2001  (GB) .................................. 0112079.9
Mar. 14, 2002  (GB) .................................. 0206010.1
Mar. 27, 2002  (GB) .................................. 0207167.8

(51) Int. Cl.
    *C30B 7/08*    (2006.01)
(52) U.S. Cl. .............................. 117/68; 117/69; 117/70; 117/925
(58) Field of Classification Search .................. 117/68, 117/69, 70, 925
    See application file for complete search history.

(56) References Cited

U.S. PATENT DOCUMENTS

| | | | | |
|---|---|---|---|---|
| 4,983,824 A | * | 1/1991 | Saaski et al. | 250/227.27 |
| 5,032,026 A | * | 7/1991 | Jouve et al. | 356/478 |
| 5,065,030 A | | 11/1991 | Perlman | |
| 5,120,131 A | | 6/1992 | Lukosz | |
| 5,371,588 A | * | 12/1994 | Davis et al. | 356/489 |
| 5,501,986 A | | 3/1996 | Ward et al. | |
| 6,100,687 A | * | 8/2000 | Weitekamp et al. | 324/300 |
| 6,127,183 A | | 10/2000 | Ivarsson et al. | |
| 2005/0019836 A1 | * | 1/2005 | Vogel et al. | 435/7.2 |

FOREIGN PATENT DOCUMENTS

| | | |
|---|---|---|
| WO | WO 98 22807 A | 5/1998 |
| WO | WO 01/36945 | 5/2001 |

* cited by examiner

*Primary Examiner*—Robert Kunemund
(74) *Attorney, Agent, or Firm*—Michael Best & Friedrich LLP

(57) ABSTRACT

The present invention relates to a method for determining crystallization in a very small amount of a material of interest (eg a chemical or biological material of interest).

24 Claims, 12 Drawing Sheets

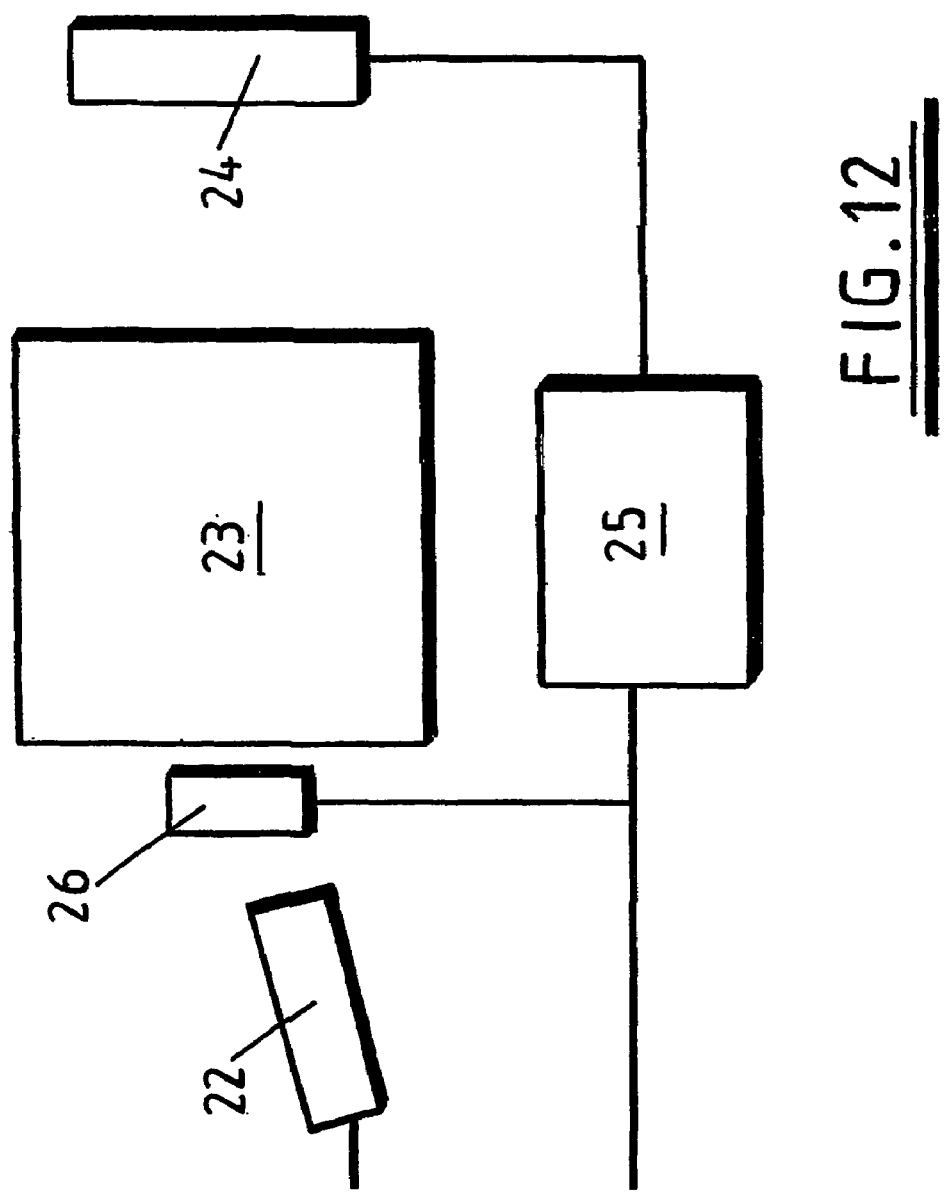

METHOD OF DETERMINING CRYSTALLIZATION

The present invention relates to a method for determining a physical mass changing event (such as crystallisation) in a material of interest (eg a chemical or biological material of interest).

Crystallography is capable of providing very important information regarding the atomic structure of crystalline materials. Protein crystallography for example is a growing area of great importance to the pharmaceutical industry and provides exquisite detail regarding the spatial relationship of atoms and also the secondary and tertiary structures adopted by such large and complex molecules. From this information the protein chemist can obtain crucial information about the structure and function of the protein which may ultimately be related to the role of the protein in the diseased or healthy state. Knowing the structure and function of the molecule also provides crucial information on the likely efficacy of new chemical entities (potential drug molecules) and helps to refine the search in the early stages of the drug discovery process.

In order to obtain an X-ray crystal structure, it is necessary firstly to obtain a high quality crystal of the material of interest. Unfortunately many materials of interest are difficult to crystallise and procedures to obtain crystals do not lend themselves to systematic investigation. As a result, the process of obtaining high quality crystals (especially in the field of proteins) is almost invariably the rate-determining step.

In recent years 'crystal farms' have been developed which are highly automated and enable numerous different conditions to be tested in an attempt to identify the correct conditions for crystallisation. Whilst this is potentially useful, the time required to elapse before the user is confident that crystallisation has had an opportunity to proceed can run into days. Moreover the supply of the material of interest (eg protein) required to fully test the potential conditions for crystallisation may be exhausted before the correct conditions are identified.

The present invention seeks to improve the determination of the mass characteristics of a material of interest by exploiting the sensitivity of certain sensor devices to physical (ie non-chemical) mass changing events at the molecular level. More particularly, the present invention relates to a method for determining a physical mass changing event in the material of interest (such as the onset of crystallisation) by measuring the temporal response of a sensor device to which the material of interest is exposed.

Thus viewed from one aspect the present invention provides a method for determining a physical mass changing event in a material of interest in a localised environment, said method comprising:

(A) providing a sensor device having a sensor component capable of exhibiting a measurable response to a change in the localised environment caused by the physical mass changing event in the material of interest therein;

(B) introducing the material of interest into the localised environment;

(C) inducing the physical mass changing event in the material of interest;

(D) generating an output from the sensor component over a temporal range;

(E) measuring the response of a characteristic of the output over the temporal range; and (F) relating the response of the characteristic of the output over the temporal range to the physical mass changing event.

The temporal response of the characteristic of the output of the sensor component depends crucially upon the type of physical mass changing event. For example, the sensor component exhibits a very different response to rapid adsorption of the material of interest onto its surface than to crystallisation of the material of interest on its surface. It is the sensitivity of the sensor component leading to the measurable variation in the temporal response which enables different physical mass changing events occurring at a molecular level to be differentiated.

The sensor component may be capable of exhibiting a measurable response in a parameter selected from effective refractive index, a dielectric constant, a viscoelastic property, a frequency of oscillation, a thermal absorption/desorption parameter, the permeability, the absorption of energy or energetic particles (such as x-rays, gamma rays, $\beta$-rays, electrons, ions, light, microwaves, acoustic waves) or the particle size. For example, the sensor device may be one or more of the following types: surface plasmon resonance sensor devices, resonant mirror sensor devices, acoustic sensor devices (such as quartz crystal and surface acoustic wave devices (by using frequency decay techniques for example)), electrical sensor devices (capable of measuring impedance at (for example) RF or microwave frequencies) or light scattering devices. Preferably the parameter is the effective refractive index.

In a preferred embodiment, step (D) comprises: (D) irradiating the sensor component with electromagnetic radiation to generate an output over a temporal range.

The physical mass changing event may be an ordered (ie non-random) physical mass changing event. In a preferred embodiment, the physical mass changing event is crystallisation.

In a preferred embodiment, step (C) comprises: imposing a condition such as to induce the physical mass changing event. Particularly preferably the method further comprises:

(G) associating the physical mass changing event with the condition. The condition may be a chosen temperature, pressure, acidity, solvent or humidity.

In a preferred embodiment, step (C) is preceded by the step of:

(C0) sequentially imposing variable conditions on the localised environment until the condition in the localised environment is such as to induce the physical mass changing event.

This embodiment advantageously permits the physical mass changing event to be rapidly associated with the condition under which it has been induced in step (C) using small amounts of the material of interest. By way of example, the embodiment advantageously permits a crystallographer to investigate a wide range of potential conditions for inducing crystallisation more rapidly and using lesser amounts of the material of interest (eg protein) than is possible with conventional methods. Having identified the precise conditions for inducing crystallisation, the potential for obtaining suitable crystal structures is significantly improved.

Before or after step (B), the method may comprise:

(1) irradiating the sensor component with electromagnetic radiation to generate a first output;

(2) measuring a characteristic of the first output; and wherein steps (E) and (F) are:

(E) measuring the response of a characteristic of the output over the temporal range relative to the characteristic of the first output; and (F) relating the response of the characteristic of the output over the temporal range relative to the characteristic of the first output to the physical mass changing event.

Steps (1) and (2) may be performed at start-up. The results may be stored electronically (eg as calibration data).

In a preferred embodiment, the sensor device is an interferometric sensor device. The sensor component of the interferometric sensor device may comprise at least one waveguide (eg a slab or channel waveguide) or a fibre optic component. For example, the sensor component may be a waveguide structure. The waveguide structure may be generally of the planar type disclosed in WO-A-98/22807 or WO-A-01/36945.

Preferably the sensor component is a waveguide structure including:

either (a) one or more sensing layers capable of inducing in a secondary waveguide a measurable response to a change in the localised environment caused by the physical mass changing event or (b) a sensing waveguide capable of exhibiting a measurable response to a change in the localised environment caused by the physical mass changing event.

In this embodiment, the mass changing event contributes to a change in the effective refractive index of the sensor component and this is advantageously exploited to differentiate mass changing events.

Particularly preferably the sensor component is a waveguide structure including:

either (a) one or more sensing layers capable of inducing in a secondary waveguide a measurable response to a change in the localised environment caused by the physical mass changing event and an inactive (eg deactivated) secondary waveguide in which the sensing layer is incapable of inducing a measurable response to a change in the localised environment caused by the physical mass changing event or (b) a sensing waveguide capable of exhibiting a measurable response to a change in the localised environment caused by the physical mass changing event and an inactive (eg deactivated) waveguide substantially incapable of exhibiting a measurable response to a change in the localised environment caused by the physical mass changing event.

Preferably each of the sensing waveguide or secondary waveguide (or any additional waveguides such as reference waveguides) of the sensor component is a planar waveguide (ie a waveguide which permits light propagation in any arbitrary direction within the plane). Particularly preferably each planar waveguide is a slab waveguide.

Preferably the sensor component constitutes a multi-layered structure (eg a laminated waveguide structure) of the types disclosed in WO-A-98/22807 and WO-A-01/36945 (Farfield Sensors Limited). In a preferred embodiment, each of the plurality of layers in the multi-layered sensor component are built onto a substrate (eg of silicon) through known processes such as PECVD, LPCVD, etc. Intermediate transparent layers may be added (eg silicon dioxide) if desired. Typically the sensor component is a multilayered structure of thickness in the range 0.2–10 microns. A layered structure advantageously permits layers to be in close proximity (eg a sensing waveguide and an inactive (reference) waveguide may be in close proximity to one another so as to minimise the deleterious effects of temperature and other environmental factors). Preferably the sensor component comprises a stack of transparent dielectric layers wherein layers are placed in close proximity. Preferably each layer is fabricated to allow equal amounts of electromagnetic radiation to propagate by simultaneous excitation of the guided modes in the structure.

The characteristic of the output may be a positional characteristic. Preferably the output is a pattern of interference fringes which may be measured (step (E)) by a conventional measuring means (see for example WO-A-98/22807) eg one or more detectors such as photodetectors which measure the intensity of electromagnetic radiation. Preferably step (E) comprises: measuring movements in the pattern of interference fringes over the temporal range. Particularly preferably step (E) further comprises: calculating the phase shift from the movements in the pattern of interference fringes over the temporal range.

The characteristic of the output may be a non-positional characteristic. In a preferred embodiment, the non-positional characteristic of the pattern of interference fringes is the contrast (eg the difference in intensity between the outer fringe envelope and the inner fringe envelope). For example, the contrast may be the difference in intensity between the outer fringe envelope and the inner fringe envelope at a corresponding position in the pattern. Preferably the contrast may be the difference in intensity between the maxima of the outer fringe envelope and the maxima of the inner fringe envelope.

The measurement of non-positional characteristics of an interference pattern is discussed in co-pending UK patent application number 0207167.8 of Farfield Sensors Limited.

Preferably the sensor component is adapted so as to be usable in evanescent mode or whole waveguide mode.

Thus in a first embodiment, the sensor component includes one or more sensing layers capable of inducing in a secondary waveguide a measurable response to a change in the localised environment caused by the physical mass changing event. In this first embodiment, the sensor device is advantageously adapted to optimise the evanescent component so as to induce in the secondary waveguide a measurable response. The sensor component may comprise a plurality of separate sensing layers to enable physical mass changing events at different localised environments to be determined.

In a preferred embodiment, the sensing layer comprises an absorbent material (eg a polymeric material such as polymethylmethacrylate, polysiloxane, poly-4-vinylpyridine) or a bioactive material (eg containing antibodies, enzymes, DNA fragments, functional proteins or whole cells). The absorbent material may be capable of absorbing a gas, a liquid or a vapour containing a chemical material of interest. The bioactive material may be appropriate for liquid or gas phase biosensing. For example, the sensing layer may comprise a porous silicon material optionally biofunctionalised with antibodies, enzymes, DNA fragments, functional proteins or whole cells.

In a preferred method of the invention, the secondary waveguide comprises silicon oxynitride or silicon nitride.

In a second embodiment, the sensor component includes a sensing waveguide capable of exhibiting a measurable response to a change in the localised environment caused by the physical mass changing event. In this second embodiment, the sensor device is adapted to minimise the evanescent component and may be used advantageously in whole waveguide mode.

In a preferred embodiment, the sensing waveguide comprises an absorbent material (eg a polymeric-material such as polymethylmethacrylate, polysiloxane, poly-4 vinylpyridine) or a bioactive material (eg containing antibodies, enzymes, DNA fragments, functional proteins or whole cells). The absorbent material may be capable of absorbing a gas, a liquid or a vapour containing a chemical material of interest. The bioactive material may be appropriate for liquid or gas phase biosensing. For example, the sensing waveguide may comprise a porous silicon material optionally biofunctionalised with antibodies, enzymes, DNA fragments, functional proteins or whole cells.

Where the sensor component comprises a sensing waveguide adapted for use in whole waveguide mode, an absorbent layer in the form of an overcoating may be present for use as a membrane (for example) to separate out certain stimuli.

To optimise the performance of the first embodiment, the sensor component may further comprise an inactive secondary waveguide in which the sensing layer is incapable of inducing a measurable response to a change in the localised environment caused by the physical mass changing event. The inactive secondary waveguide is capable of acting as a reference layer. It is preferred that the secondary waveguide and inactive secondary-waveguide have identical properties with the exception of the response to the change in the localised environment caused by the physical mass changing event. By way of example, the secondary waveguide and inactive secondary waveguide are made of silicon oxynitride.

To optimise the performance of the second embodiment, the sensor component may further comprise an inactive (eg deactivated) waveguide substantially incapable of exhibiting a measurable response to a change in the localised environment caused by the physical mass changing event. The inactive waveguide is capable of acting as a reference layer. The physical, biological and chemical properties of the sensing waveguide and inactive waveguide are as similar as possible (with the exception of the response to the change in the localised environment caused by the physical mass changing event). Typically the inactive waveguide is made of silicon oxynitride.

As a consequence of mass changing events, changes in the dielectric properties (eg the effective refractive index) of the sensing waveguide or sensing layer occur. This causes a measurable response (ie a change in the transmission of electromagnetic radiation down the sensing waveguide (or waveguides) in whole waveguide mode or the secondary waveguide in evanescent field mode) which (in one embodiment) manifests itself as a movement of interference fringes. This differs according to whether the sensor component is interrogated in TE or TM mode.

By way of example, the movement of the pattern of interference fringes may be used to calculate the phase shift which takes place in the sensing waveguide or sensing layer during the passage of electromagnetic radiation through the sensor component. The phase shift is effectively directly proportional to changes occurring in the effective refractive index of the sensing waveguide or sensing layer and differs according to whether the sensor component is interrogated in TE or TM mode.

A pattern of interference fringes (eg for TE and TM modes respectively) may be generated when the electromagnetic radiation from the sensor component is coupled into free space and may be recorded in a conventional manner (see for example WO-A-98/22807). A response of the sensor component to a change in the localised environment may be measured from movement of the fringes in the interference pattern. The phase shift of the electromagnetic radiation in the sensor component (eg induced in the secondary waveguide in evanescent field mode or exhibited in the sensing waveguide in whole waveguide mode) may be calculated.

Movement in the interference fringes may be measured either using a single detector which measures changes in the intensity of electromagnetic radiation or a plurality of such detectors which monitor the change occurring in a number of fringes or the entire interference pattern. The one or more detectors may comprise one or more photodetectors (eg photodiodes). Where more than one photodetector is used this may be arranged in an array. In an array format, the relating means capable of relating the measurable response in TM mode and the measurable response in TE mode to a physical mass changing event may be deployed in a spatially resolved manner. Such spatial resolution can be achieved by means of (for example) remote imaging or lithography or scanning a measurement probe as in the case of an atomic microprobe.

In a preferred embodiment of the method of the invention, step (D) is carried out with electromagnetic radiation in TM mode.

In a preferred embodiment of the method of the invention, step (D) is carried out with electromagnetic radiation in TE mode.

In a preferred embodiment of the method of the invention, step (D) comprises:

(D1) irradiating the sensor component with electromagnetic radiation in TE mode to produce a first pattern of interference fringes;

(D2) irradiating the sensor component with electromagnetic radiation in TM mode to produce a second pattern of interference fringes; and step (E) comprises:

(E1) measuring movements in the first pattern of interference fringes; and (E2) measuring movements in the second pattern of interference fringes.

Particularly preferably step (E) of the method of the invention further comprises:

(E3) calculating the phase shift of the sensor component in TM mode from the movements in the first pattern of interference fringes;

(E4) calculating the phase shift of the sensor component in TE mode from the movements in the second pattern of interference fringes;

and step (F) is relating the phase shift of the sensor component in TM mode and the phase shift of the sensor component in TE mode to the physical mass changing event.

More preferably step (E) of the method of the invention further comprises:

(E3) calculating the phase shift of the sensor component in TM mode from the movements in the first pattern of interference fringes (E4) calculating the phase shift of the sensor component in TE mode from the movements in the second pattern of interference fringes;

(E5) calculating the phase shift of the sensor component in TM mode relative to the phase shift of the sensor component in TE mode;

and step (F) is relating the phase shift of the sensor component in TM mode relative to the phase shift of the sensor component in TE mode to the physical mass changing event.

Preferably the phase shift of the sensor component in TM mode relative to the phase shift of the sensor component in TE mode is a ratio of the phase shift of the sensor component in TM mode to the phase shift of the sensor component in TE mode.

Step (D) may comprise: generating an output from the sensor component on at least two occasions over a temporal range. Preferably step (D) comprises: generating an output from the sensor component continuously over a temporal range.

The physical mass changing event is typically determined qualitatively but may be determined quantitatively.

In a preferred embodiment of the method, said sensor device further comprises:

first irradiating means for irradiating the sensor component with electromagnetic radiation in TM mode;

second irradiating means for irradiating the sensor component with electromagnetic radiation in TE mode;

measuring means for measuring the measurable response of the sensor component in TM mode and for measuring the measurable response of the sensor component in TE mode; and relating means capable of relating the measurable response of the sensor component in TM mode and the measurable response of the sensor component in TE mode to the physical mass changing event.

The first and second irradiating means may be the same or different. The measuring means may be one or more detectors in an array.

Preferably the sensor device further comprises: a synchronising means for synchronising the measuring means with the first irradiating and second irradiating means so as to correlate the measurement of the measurable response of the sensor component in TE mode and of the measurable response of the sensor component in TM mode with the irradiation of the sensor component with electromagnetic radiation in TE and TM mode respectively.

Particularly preferably the synchronising means is capable of calculating the phase shift of the sensor component in TE mode and the phase shift of the sensor component in TM mode.

Particularly preferably the synchronising means is capable of relating the movements in the first pattern of interference fringes and second pattern of interference fringes to the physical mass changing event.

The first and second irradiating means may be adapted to irradiate the sensor component with electromagnetic radiation in TE or TM mode sequentially or simultaneously. The first and second irradiating means may be the same or different. Where different sources of electromagnetic radiation are used, an optical switch (eg a rotating mirror) may be used to switch rapidly between the two. Alternatively, a single source of electromagnetic radiation may be used to simultaneously excite TE and TM modes of the sensor component by (for example) aligning the polarisation vector of the linearly polarised source at an angle with respect to the plane of the sensing waveguide or sensing layer of the sensor component. An active analyser system may be used to alternately remove the unwanted TE or TM mode radiation during data capture of the desired TM or TE output respectively. The active analyser system may comprise an electro-optic half wave plate placed in series with an analyser.

In a preferred embodiment, an adjustable analyser may be used to measure the first pattern of interference fringes and the second pattern of interference fringes separately. The measurements may be synchronised with the excitation and/or polarisation procedure to ensure that phase shift information is correlated with TE and TM excitation.

A controller may be provided to synchronise the one or more sources of electromagnetic radiation and one or more detectors. For example, the controller may capture the data from a photodetector (eg photodiode) array. The firing of the (or each) source of electromagnetic radiation may be synchronised by the controller with the alternate capture of the first and second pattern of interference fringes generated in TM mode and TE mode. The controller may be adapted to calculate the phase shift in TE and TM modes independently.

Electromagnetic radiation generated from a conventional source may be propagated into the sensor component in a number of ways. In a preferred embodiment, electromagnetic radiation is simply input via an end face of the sensor component (this is sometimes described as Aan end firing procedure@). Preferably the electromagnetic radiation source provides incident electromagnetic radiation having a wavelength falling within the optical range. Propagating means may be employed for substantially simultaneously propagating incident electromagnetic radiation into a plurality of waveguides. For example, one or more coupling gratings or mirrors may be used. A tapered end coupler rather than a coupling grating or mirror may be used to propagate radiation into the lowermost waveguide. Preferably the amount of electromagnetic radiation in the sensing waveguide/inactive waveguide or in the secondary waveguide/inactive secondary waveguide is equal.

The incident electromagnetic radiation may be oriented (eg plane polarised) as desired using an appropriate polarising means. The incident electromagnetic radiation may be focussed if desired using a lens or similar micro-focussing means.

A plurality of electromagnetic radiation detector units (eg in an array) and/or a plurality of electromagnetic radiation sources may be used to measure in discrete areas of the sensor component simultaneously the responses to changes in the localised environment caused by the mass changing event. Alternatively, the position of the electromagnetic radiation detector and electromagnetic radiation source relative to the sensor component may be changed to provide information concerning responses in discrete areas of the sensor component. For example, discrete responses to a change in the localised environment caused by different physical mass changing events may be measured in discrete areas of the sensor component. For this purpose, the preferred assembly makes use of the versatility of the evanescent mode and comprises a plurality of separate sensing layers or regions.

The sensor component may be excited across its width and a two-dimensional photodiode array (or the like) may be used to effectively interrogate Astrips@ of the sensor component (eg an array sensor). This may be carried out across more than one axis simultaneously or sequentially to provide spatially resolved information relating to physical mass changing events on the sensor component.

Preferably the sensor device comprises:

means for intimately exposing at least a part of the (or each) sensing layer or the sensing waveguide of the sensor component to the localised environment.

In a preferred embodiment, the means for intimately exposing at least a part of the sensing layer or the sensing waveguide to the localised environment is integrated onto the sensor component.

Preferably the means for intimately exposing at least a part of the (or each) sensing layer or the sensing waveguide of the sensor component to the localised environment is as described in WO-A-01/36945. The means may be automated in order to reduce the requisite degree of user intervention.

Preferably the means for intimately exposing at least a part of the sensing layer or the sensing waveguide to the localised environment is adapted to induce physical mass changing events in a static analyte containing a chemical or biological material of interest. In this sense, the system may be considered to be dynamic. Physical mass changing events may be induced in any conventional manner such as by heat or radiation.

The means for intimately exposing at least a part of the (or each) sensing layer or the sensing waveguide to the localised environment may be a part of a microstructure positionable on the surface of and in intimate contact with the sensor component.

Preferably the microstructure comprises means for intimately exposing at least a part of the sensing layer or the sensing waveguide to the localised environment in the form of one or more microchannels and/or microchambers. For example, an analyte containing a chemical material of interest may be fed through microchannels or physical mass changing events may take place in an analyte containing a material of interest located in a microchamber. An analyte containing chemical material of interest may be fed into the microchannels by capillary action or positively fed by an urging means.

In a preferred embodiment, the means for intimately exposing at least a part of the (or each) sensing layer or the sensing waveguide to the localised environment is included in a cladding layer. For example, microchannels and/or microchambers may be etched into the cladding layer. The cladding layer may perform optical functions such as preventing significant discontinuities at the boundary of the sensing waveguide or sensing layer(s) or chemical functions such as restricting access of certain species to the sensing waveguide or sensing layer(s). The cladding layer may be integrated onto the sensor component.

Preferably the whole of or a portion of any additional functionality may be included in the cladding layer. In one embodiment, the sensing layer itself may be incorporated in the cladding layer (for example in the form of an absorbent material). Particularly preferably, the whole of the additional functionality may be provided in the cladding layer and include sensing devices such as for example quadrature electric field tracks or other microfluidic sensing devices. The cladding layer may incorporate an electromagnetic source (eg a laser) and/or means for detecting electromagnetic radiation (of the type detailed below). The cladding layer may incorporate a chemical separating means (eg an HPLC based device).

Preferably the means for exposing at least a part of the (or each) sensing layer or the sensing waveguide of the sensor component to the localised environment is a sensor cell. Preferably the sensor cell has a low volume (eg 50 microlitres or less). By keeping the cell volume small, the method of the invention is not hampered and the amount of protein consumed is advantageously minimised.

The present invention will now be described in a non-limitative sense with reference to the Examples and accompanying Figures in which:

FIG. 12 represents schematically in plan view a sensor device used in an embodiment of the invention.

Figure 1:
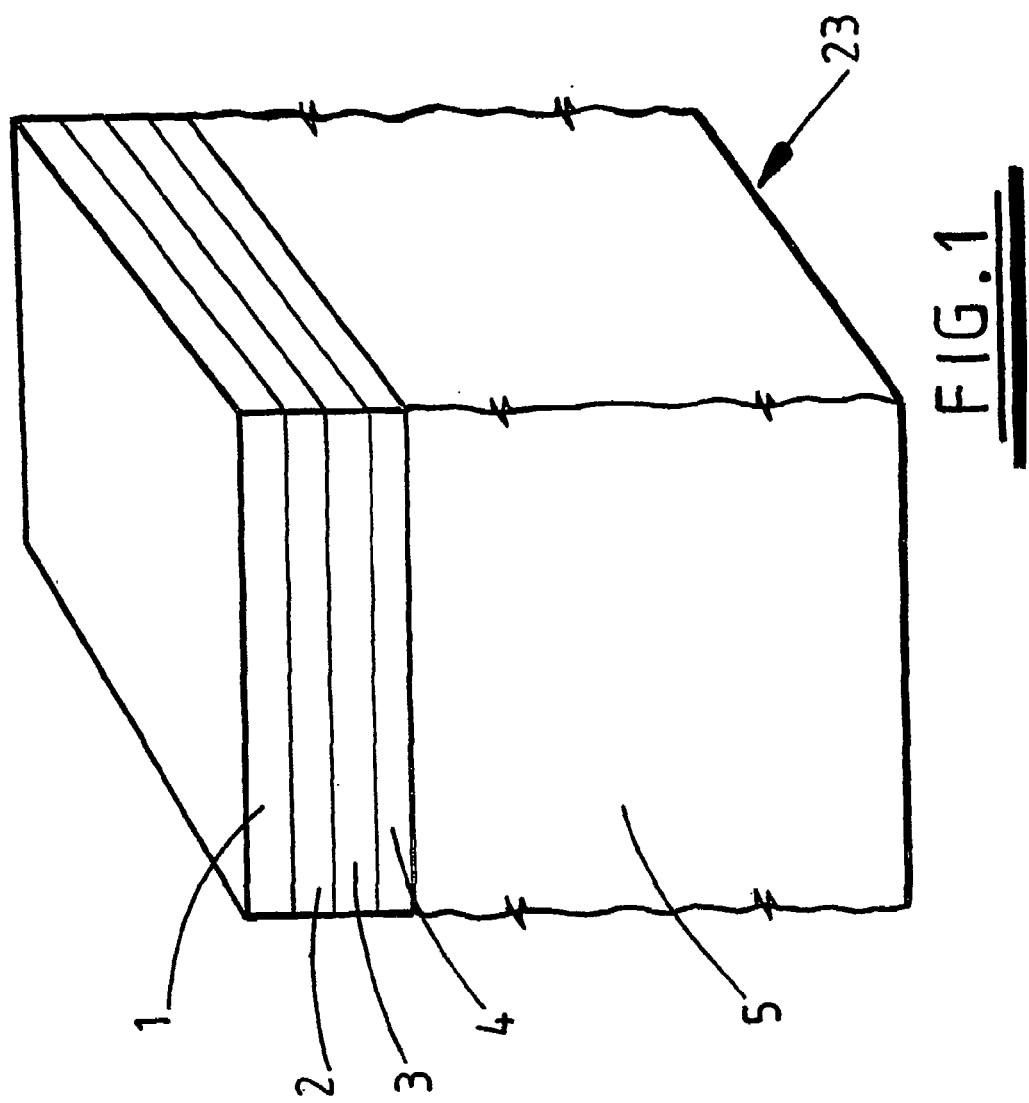
FIG. 1 illustrates schematically the sensor component used in the Examples.

An interferometric sensor component (23) of a sensor device used in the following Examples is illustrated in FIG. 1 and is of the type referred to in WO-A-98/22807. The interferometrid sensor component (23) is a laminate structure consisting of an absorbent sensing layer (1) separated from a reference waveguide (3) by a silicon dioxide spacer (2). A further silicon dioxide spacer (4) separates the silicon oxynitride reference waveguide (3) from a substrate (5) of silicon. The sensor device is shown schematically in FIG. 2 in which a rotating mirror (26) is employed to switch rapidly between electromagnetic radiation in TE and TM mode from an electromagnetic radiation source (22) for irradiating sensor component (23). A controller (25) is arranged to synchronise the rotating mirror (26) and a photodiode array (24).

EXAMPLE

The sensor component (23) of FIG. 1 was subjected to a model protein crystallisation system under a range of conditions in which the behaviour of the protein (lysozyme) was known. The crystallisation system is capable of remaining in solution, precipitating or crystallising depending upon the prevailing conditions and the temporal characteristics of each state were compared.

(1) Conditions for Non-Crystallising, Non-Aggregating Protein

A 50/50 (volume) solution of 40 mg/ml lysozyme dissolved in acetate (pH 5.5) and 2.5% salt solution in water was prepared. The solution was injected into the sensor cell at a flow rate of 0.1 ml/min. The flow was stopped after about 5 minutes which was the time it took for the solution to fill the sensor cell. The solution was left in a stationary state over the sensor device for more than three days.

Figure 2:
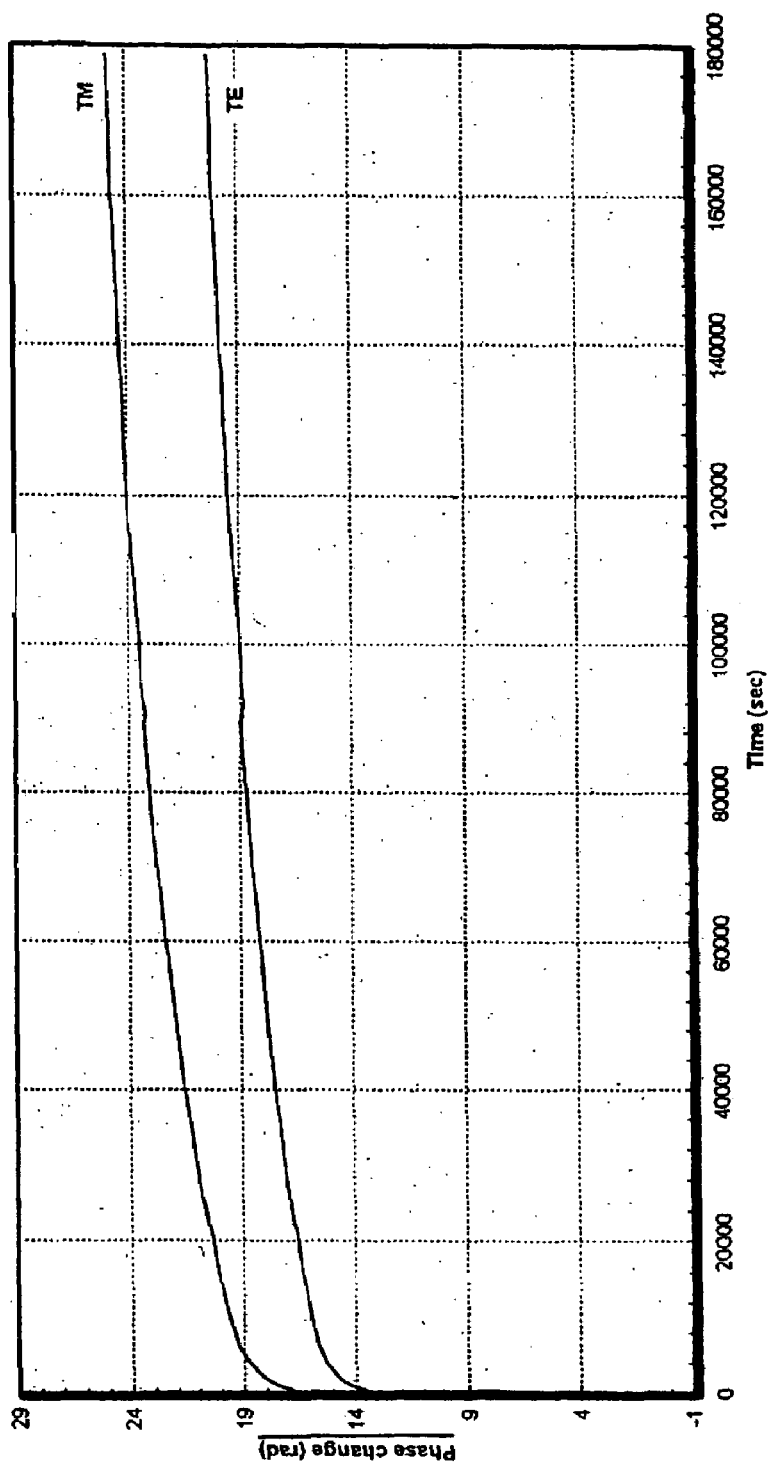
FIGS. 2–10 illustrate the temporal response of the sensor component of FIG. 1 to various physical mass changing events.
Figure 3:
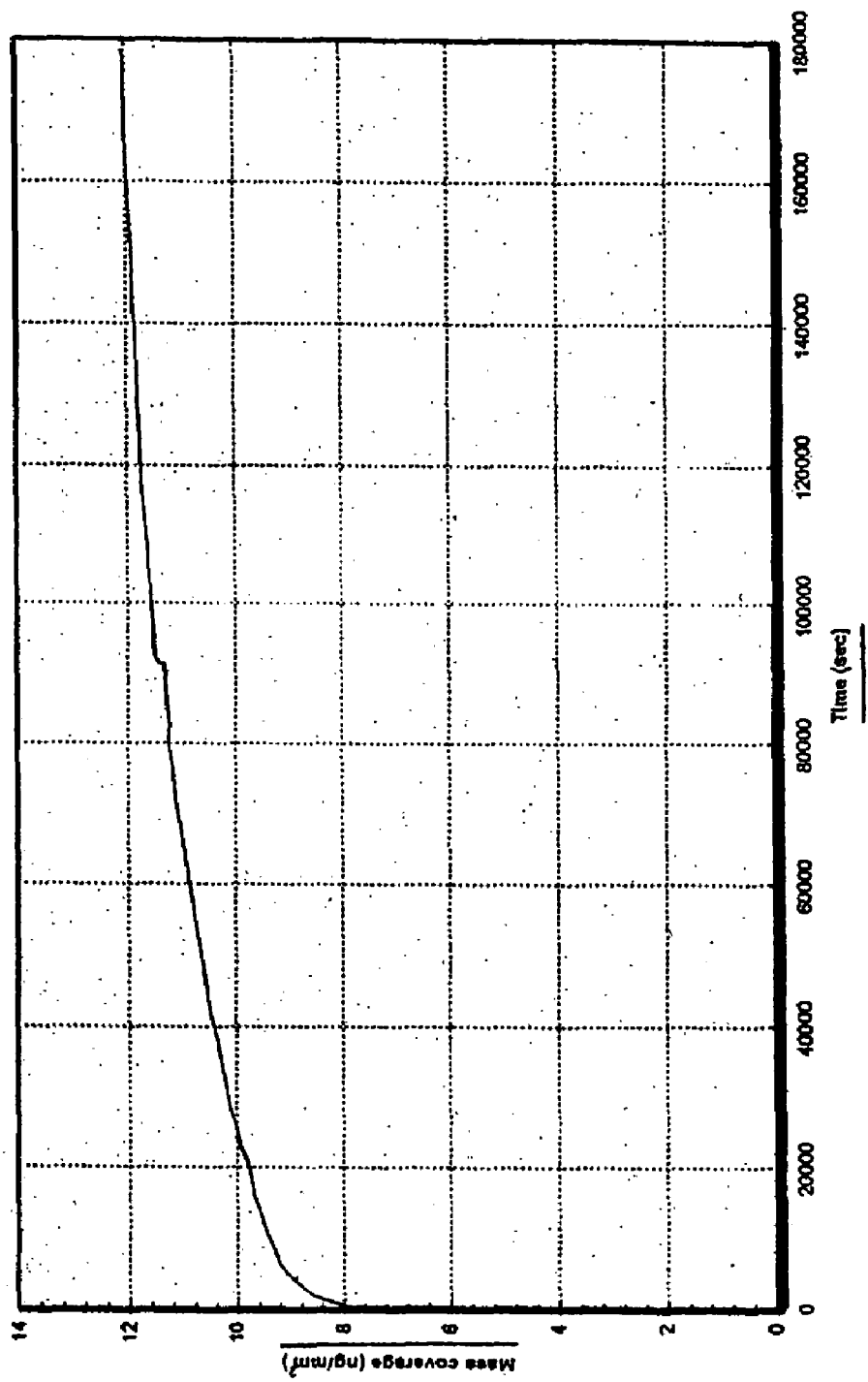
Figure 4:
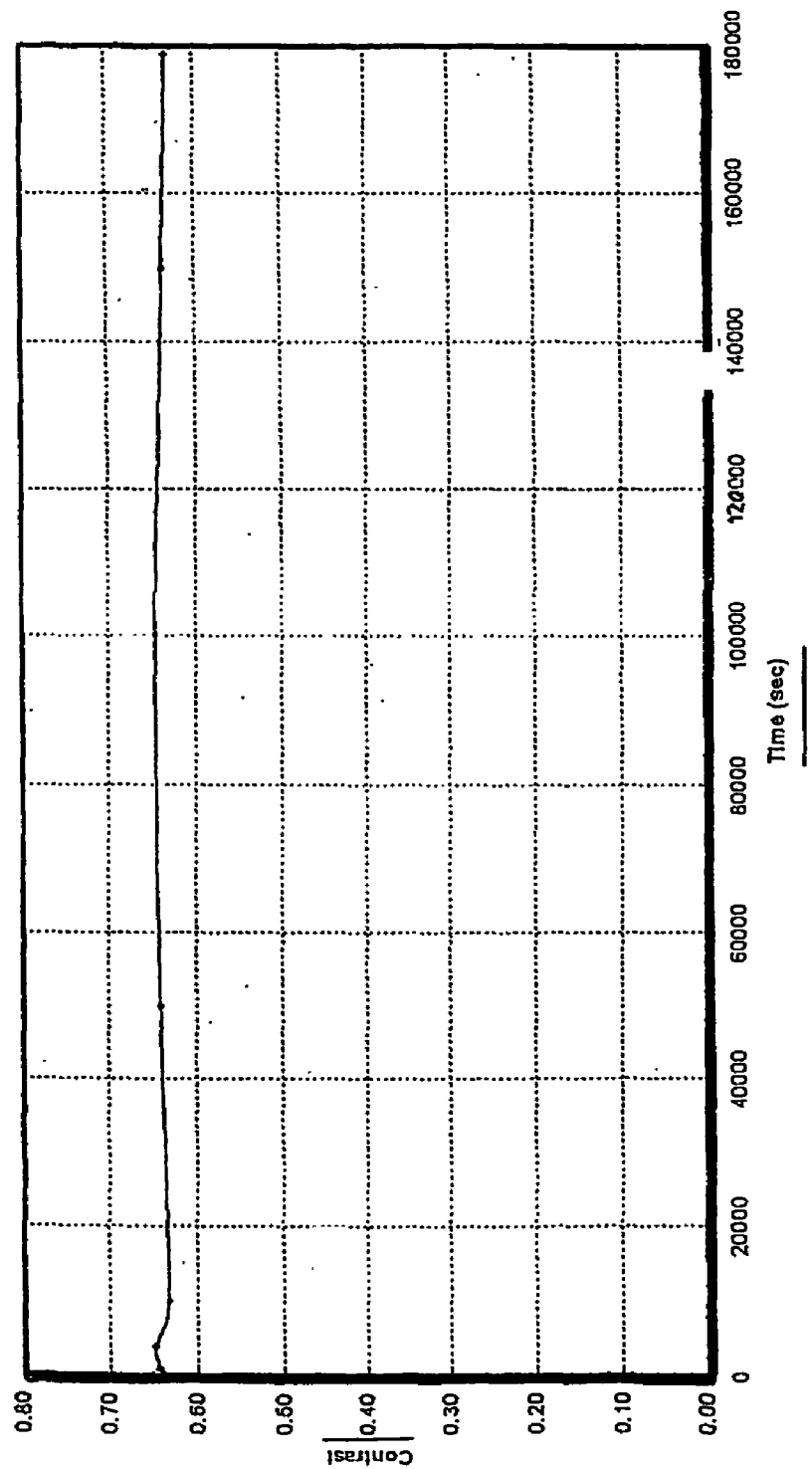

FIG. 2 shows how the phase changes (between the upper and lower waveguide (1) and (3)) in both TE and TM polarisations (a single measure of either TE or TM polarisation response could be approximated to mass changing events). This was related directly to mass changes (see FIG. 3). From these results it can be deduced that there is a steady adsorption of protein onto the surface of the sensor component. The contrast of the fringe image from the TM polarisation demonstrated very little change over the course of the experiment (see FIG. 4). Standard solutions were used to confirm that neither crystallisation nor aggregation and/or precipitation occurred under these conditions.

(2) Conditions for Precipitation

A 40 mg/ml solution of ∃-LG protein in 50 mM sodium acetate (pH 2.5) was used. To avoid precipitation prior to injecting the solution into the sensor cell, the protein powder was added to the acetate buffer in small quantities. The flow was stopped after about 5 minutes which was the time it took for the solution to fill the sensor cell. The solution was left in a stationary state over the sensor device for approximately five hours.

Figure 5:
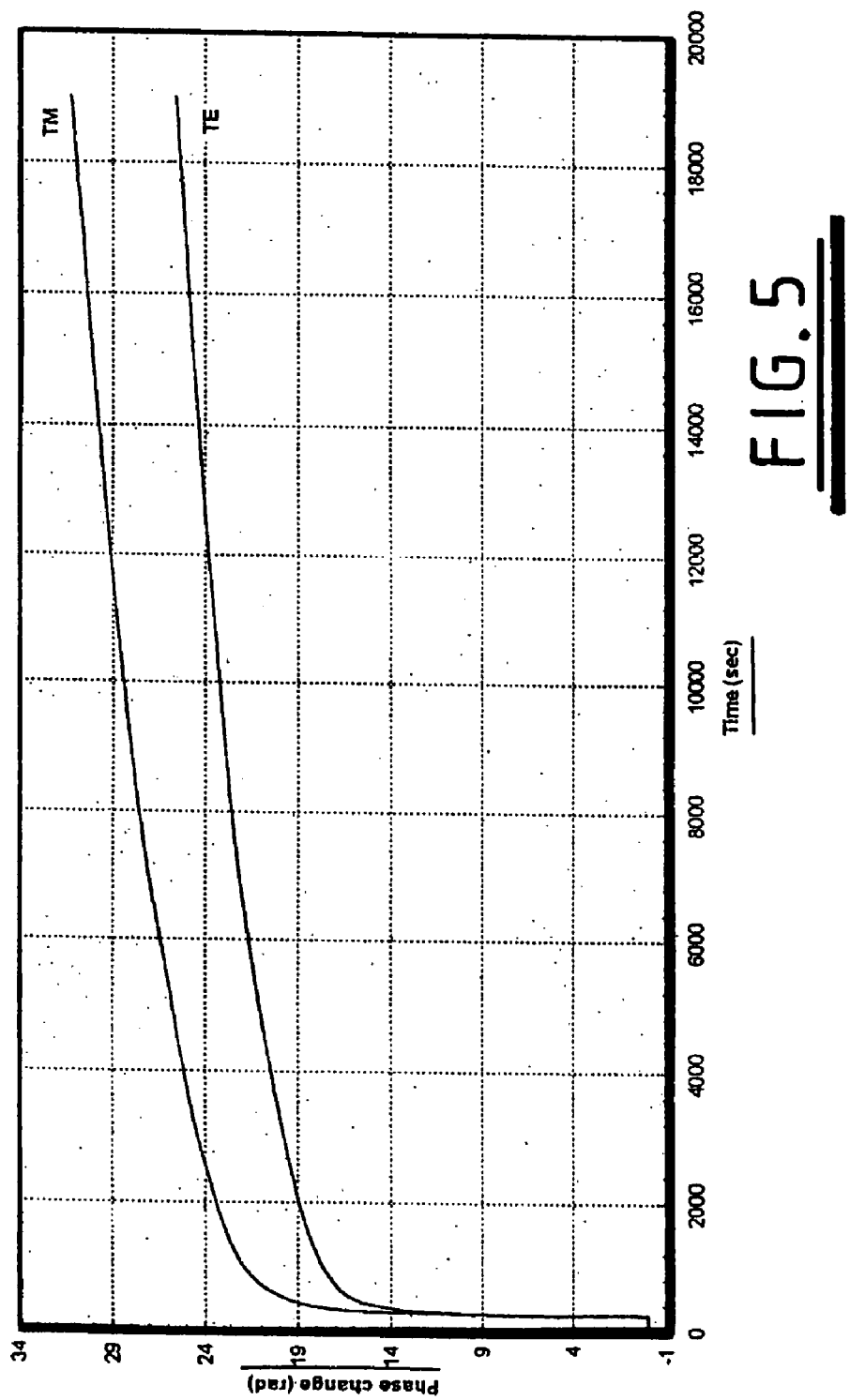
Figure 6:
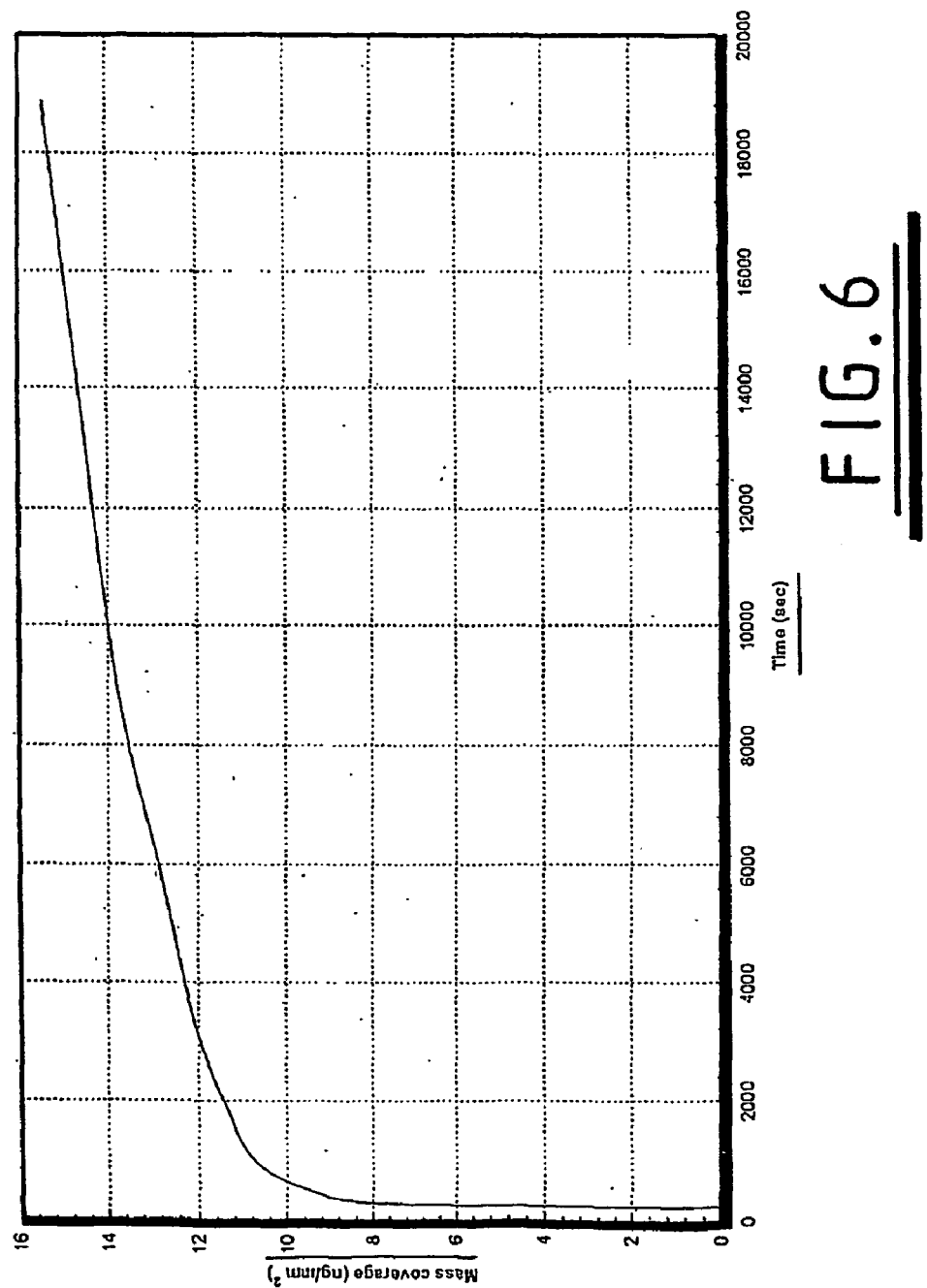
Figure 7:
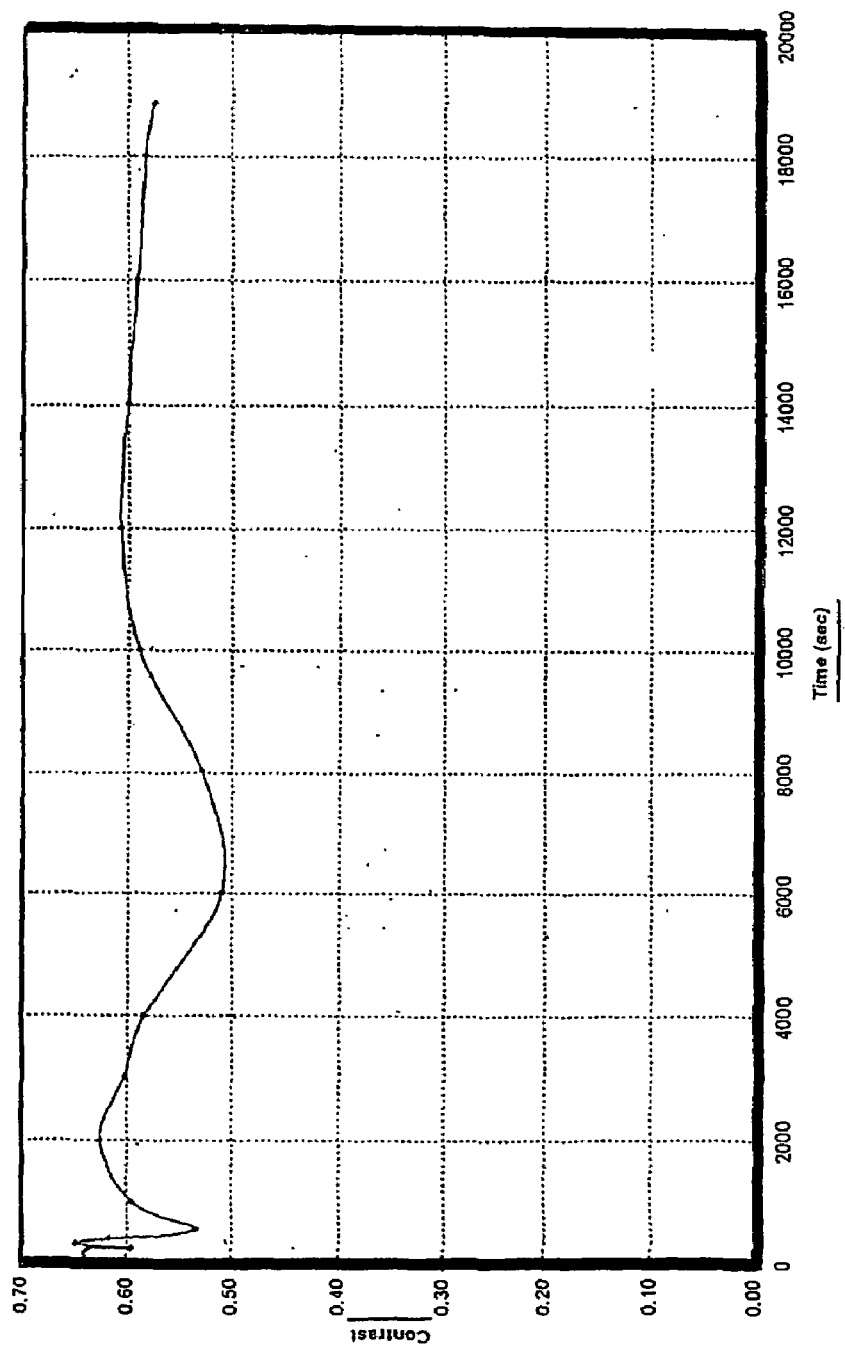

FIG. 5 shows how the phase change in TE and TM polarisations (a single measure of either TE or TM polarisation response could be approximated to mass changing events on the sensor component) occurs during aggregation. There is a steady (almost monotonic) rise in phase change during the course of the experiment. This is related directly to mass changes in FIG. 6. However it is clear that the temporal characteristics are different than under non-crystallising, non-precipitating conditions. Although there is very little change in the fringe contrast from the TM polarisation (FIG. 7), the overall profile differs from that obtained under non-crystallising, non-precipitating conditions. Solutions in standard crystallising dishes confirmed that precipitation occurred under these conditions.

(3) Conditions for Crystallisation

A 50/50 (in volume) solution of 40 mg/ml of lysozyme dissolved in acetate pH 5.5 and 10% salt solution in water was prepared. The solution was injected into the sensor cell at a flow rate of 0.1 ml/min. The flow was stopped after about 5 minutes which was the time it took for the solution to fill the sensor cell. The solution was left in a stationary state over the sensor for more than two days.

Figure 8:
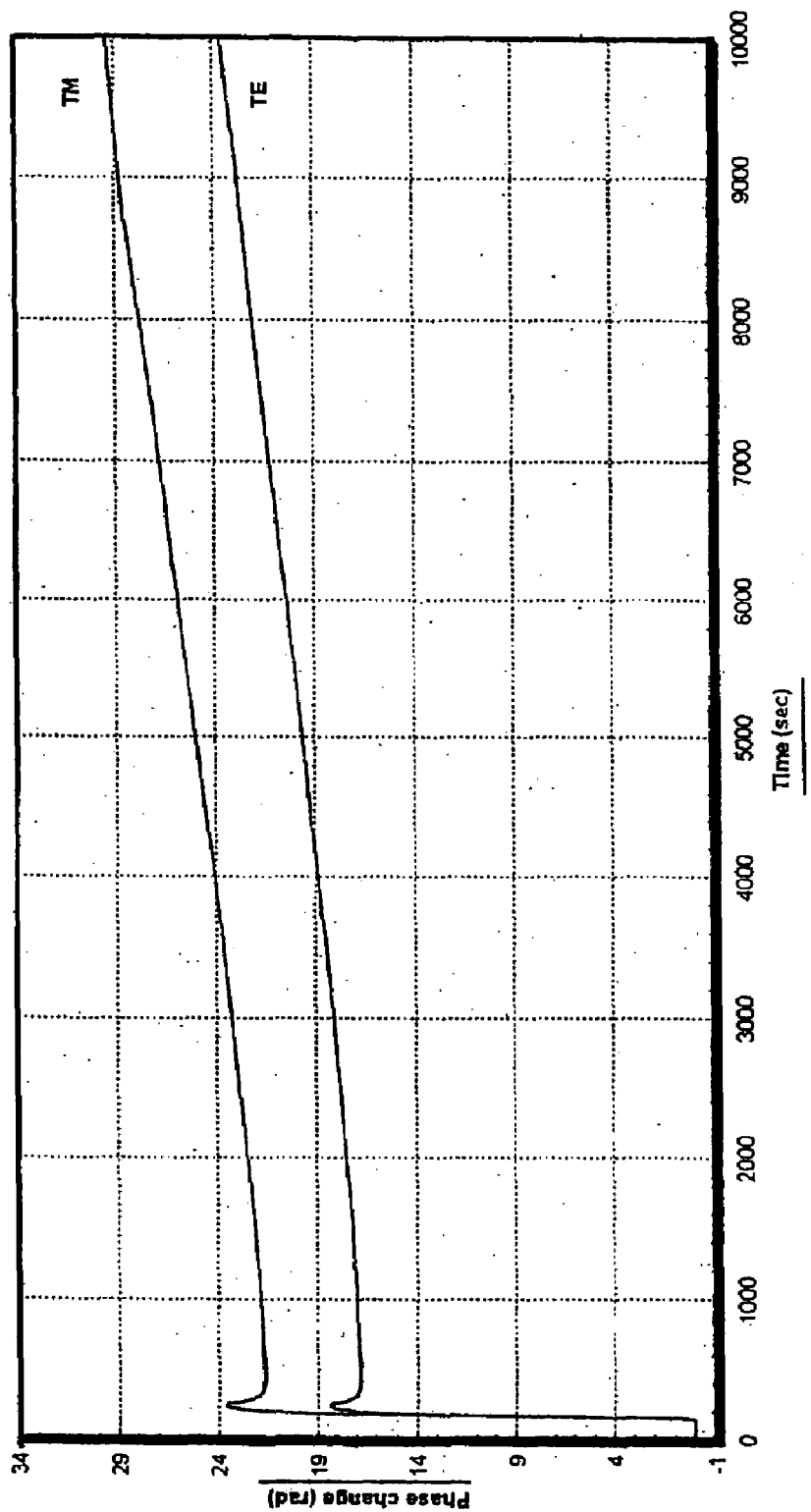
Figure 9:
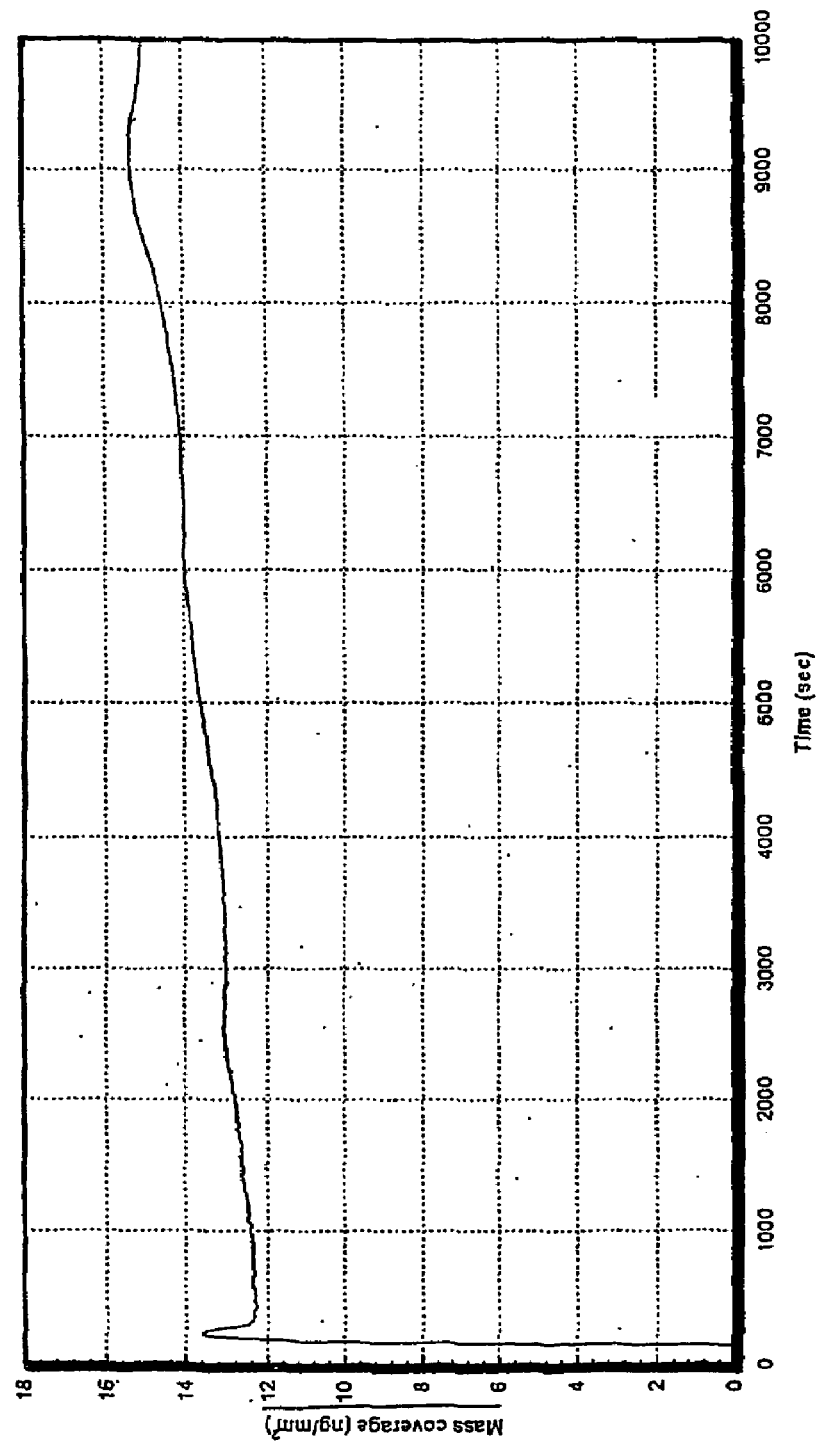
Figure 10:
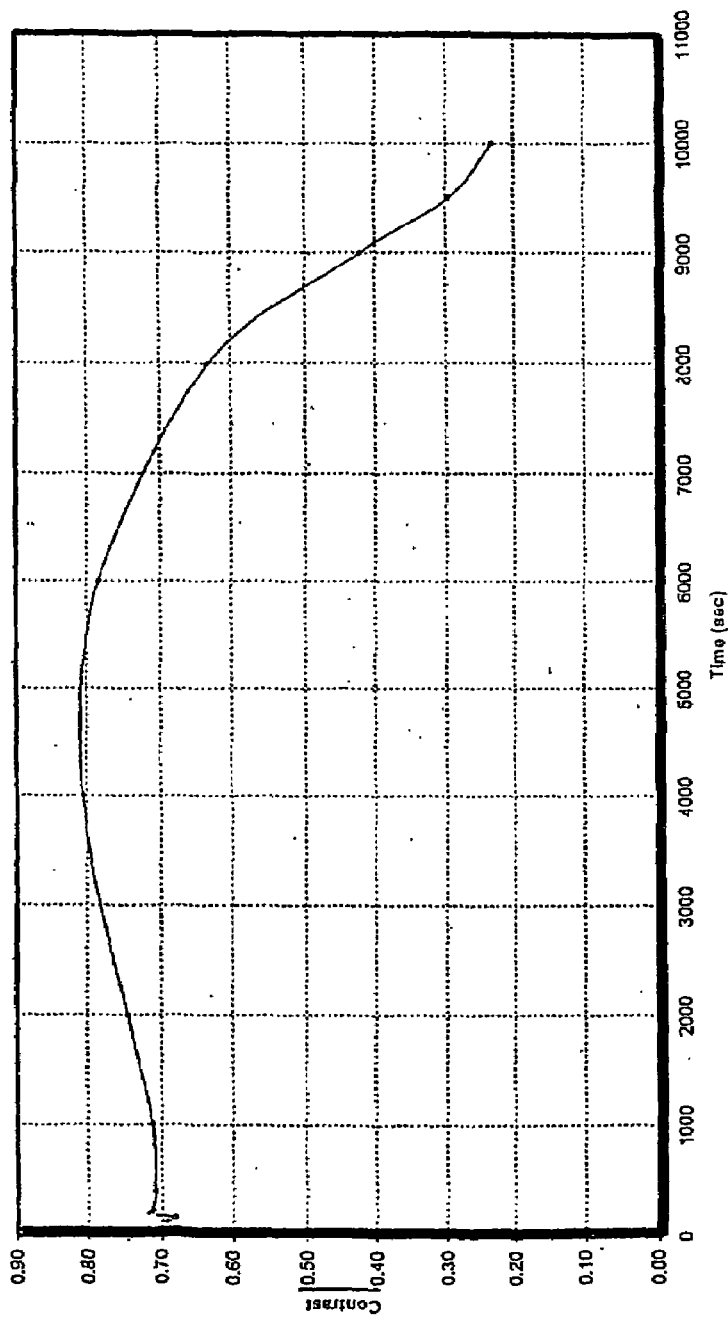

FIG. 8 shows how the TE and TM polarisations change (a single measure of either TE or TM polarisation response could be approximated to mass changing events on the sensor component) during the course of the experiment. The response was very different from both of those observed under the conditions described above for non crystallisation, non-precipitation and crystallisation respectively. These responses were directly related to mass changes (FIG. 9). In addition, the fringe image contrast from the TM polarisation demonstrates that there is a dramatic change in the output from the two waveguides (1) and (3) leading to a large diminution in contrast (FIG. 10).

Figure 11:
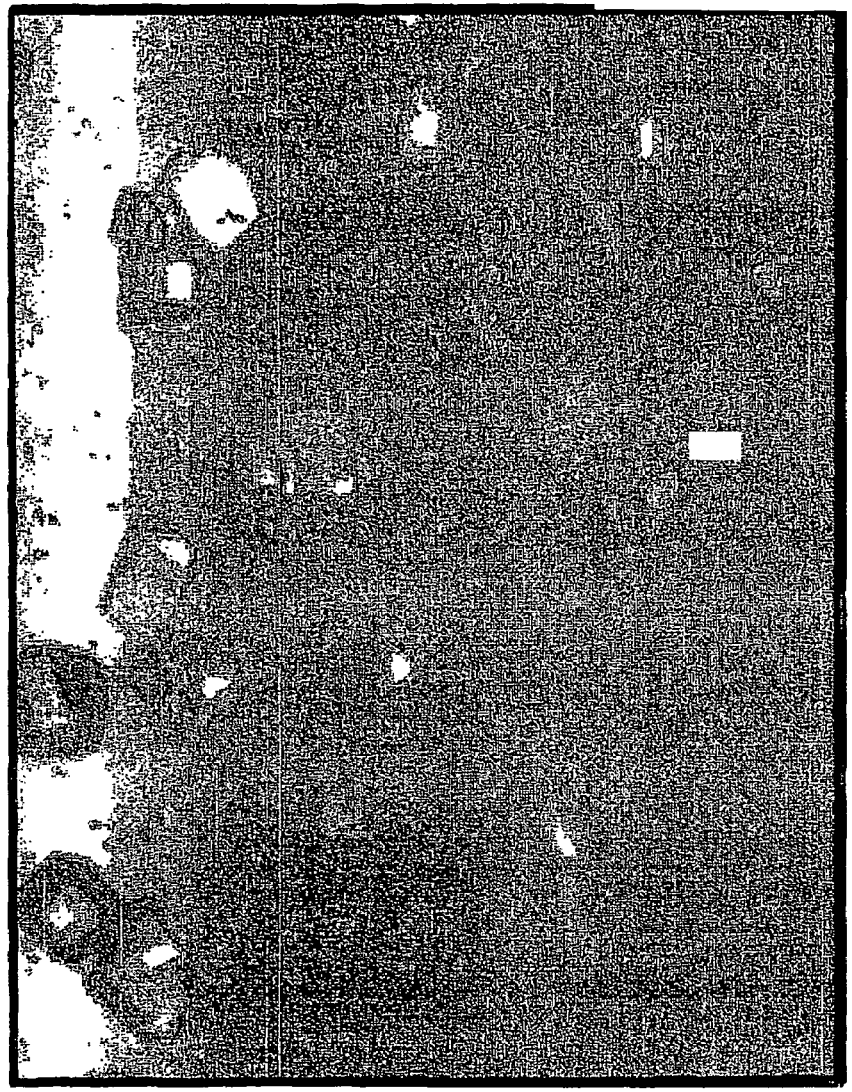
FIG. 11 illustrates the crystallisation of lysozyme under specific conditions.

Crystals were photographed after the experiment on the surface of the sensor component (FIG. 11) and solutions in standard crystallising dishes also confirmed that crystallisation occurred under these conditions.

The invention claimed is:

1. A method for determining a crystallisation in a material of interest in a localised environment, said method comprising:
   (A) providing a sensor device having an optical waveguide capable of exhibiting a measurable response to a change in the localised environment caused by the crystallisation in the material of interest therein;
   (B) introducing the material of interest into the localised environment;
   (C) inducing the crystallisation in the material of interest;
   (D) generating an output from the optical waveguide over a temporal range;
   (E) measuring the response of a characteristic of the output over the temporal range; and
   (F) relating the response of the characteristic of the output over the temporal range to the crystallisation.

2. A method as claimed in claim 1 wherein step (D) comprises: irradiating the optical waveguide with electromagnetic radiation to generate an output over a temporal range.

3. A method as claimed in claim 1 wherein step (C) comprises: imposing a condition such as to induce the crystallisation.

4. A method as claimed in claim 3 further comprising: (G) associating the crystallization with the condition.

5. A method as claimed in claim 3 wherein the condition comprises at least one of a chosen temperature, pressure, acidity, solvent, humidity and a combination thereof.

6. A method as claimed in claim 3 wherein step (C) is preceded by the step of:
   (CO) sequentially imposing variable conditions on the localised environment until the condition in the localised environment is such as to induce the crystallisation.

7. A method as claimed in claim 1 wherein the material of interest contains a biological molecule.

8. A method as claimed in claim 1 wherein the material of interest comprises a protein.

9. A method as claimed in claim 1 wherein the sensor device comprises an interferometric sensor device.

10. A method as claimed in claim 9 wherein the optical waveguide has a structure which includes:
    either (a) one or more sensing layers capable of inducing in a secondary waveguide a measurable response to a change in the localised environment caused by the crystallisation
    or (b) a sensing waveguide capable of exhibiting a measurable response to a change in the localised environment caused by the crystallisation.

11. A method as claimed in claim 9 wherein the optical waveguide has a structure which includes: either (a) one or more sensing layers capable of inducing in a secondary waveguide a measurable response to a change in the localised environment caused by the crystallisation and an inactive secondary waveguide in which the sensing layer is incapable of inducing a measurable response to a change in the localised environment caused by the crystallisation or (b) a sensing waveguide capable of exhibiting a measurable response to a change in the localised environment caused by the crystallisation and an inactive waveguide substantially incapable of exhibiting a measurable response to a change in the localised environment caused by the crystallisation.

12. A method as claimed in claim 10 wherein each of the sensing waveguide or secondary waveguide of the sensor component is a planar waveguide.

13. A method as claimed in claim 1 wherein the crystallisation contributes to a change in the effective refractive index of the optical waveguide.

14. A method as claimed in claim 9 wherein the characteristic of the output is a non-positional characteristic.

15. A method as claimed in claim 14 wherein the nonpositional characteristic is contrast of a pattern of interference fringes.

16. A method as claimed in claim 2 wherein step (D) is carried out with electromagnetic radiation in TM mode.

17. A method as claimed in claim 2 wherein step (D) is carried out with electromagnetic radiation in TE mode.

18. A method as claimed in claim 10 wherein the sensor device further comprises: means for intimately exposing at least a part of the (or each) sensing layer or the sensing waveguide of the optical waveguide, said means having a volume of 50 microlitres or less.

19. A method as claimed in claim 1 wherein step (D) comprises: generating an output from the optical waveguide on at least two occasions over a temporal range.

20. A method as claimed in claim 19 wherein step (D) comprises: generating an output from the optical waveguide continuously over a temporal range.

21. A method as claimed in claim 1, wherein the change of an optical property comprises a change of an optical property of the waveguide.

22. A method as claimed in claim 21, wherein the change of the optical property of the waveguide comprises a change in the proportion of an electromagnetic radiation which is lost during propagation of the electromagnetic radiation along the waveguide.

23. A method as claimed in claim 1, wherein the sensor comprises an interferometric sensor.

24. A method as claimed in claim 23, wherein the sensor further comprises a reference waveguide.

* * * * *